US00PP24691P3

(12) United States Plant Patent
Kerley et al.

(10) Patent No.: US PP24,691 P3
(45) Date of Patent: Jul. 22, 2014

(54) ***PRIMULA* PLANT NAMED 'KERBELRED'**

(50) Latin Name: *Primula vulgaris*
Varietal Denomination: KERBELRED

(76) Inventors: David Kerley, Cambridge (GB); Priscilla Grace Kerley, Cambridge (GB); Timothy Edward Kerley, Cambridge (GB)

( * ) Notice: Subject to any disclaimer, the term of this patent is extended or adjusted under 35 U.S.C. 154(b) by 83 days.

(21) Appl. No.: 13/507,693

(22) Filed: Jul. 20, 2012

(65) Prior Publication Data

US 2014/0026278 P1 Jan. 23, 2014

(51) Int. Cl.
*A01H 5/00* (2006.01)

(52) U.S. Cl.
USPC ..... Plt./472

(58) Field of Classification Search
USPC ..... Plt./472
See application file for complete search history.

*Primary Examiner* — Susan McCormick Ewoldt
(74) *Attorney, Agent, or Firm* — Cassandra Bright

(57) ABSTRACT

A new and distinct *Primula vulgaris* cultivar named 'KERBELRED' is disclosed, characterized, deep red, large double flowers, with enlarged sepals, strong peducles, and early blooming. Plants have shown the ability to be propagated by tissue culture at a good rate. The new variety is a *Primula vulgaris,* suitable for outdoor landscape and container use.

2 Drawing Sheets

Figure 1:
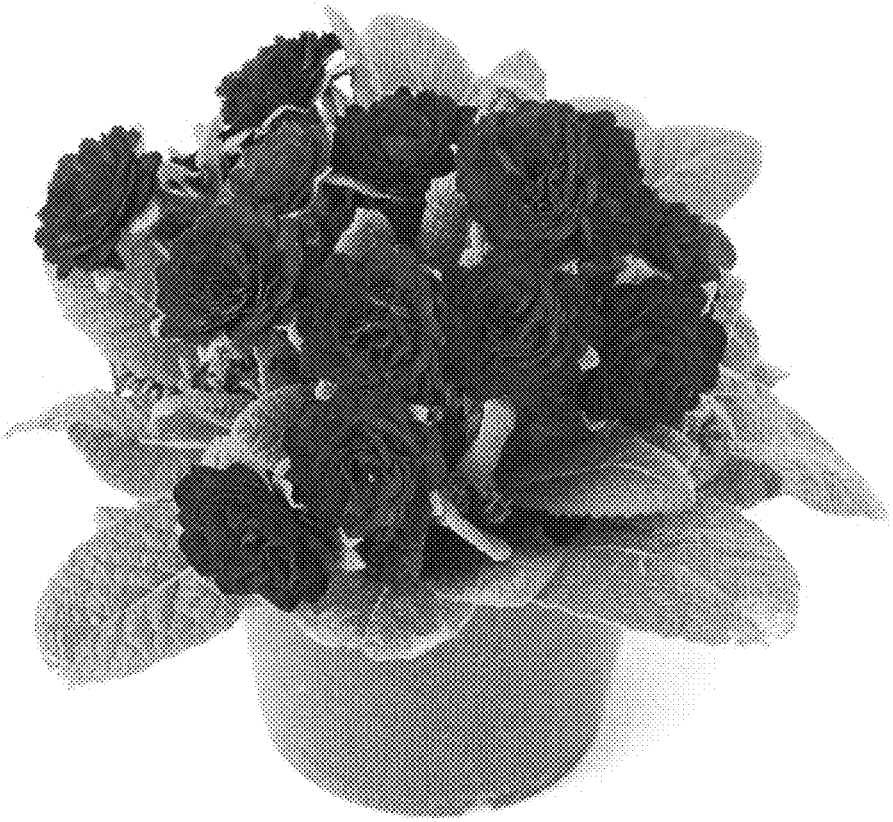

Latin name of the genus and species: *Primula vulgaris.*
Variety denomination: 'KERBELRED'.

BACKGROUND OF THE INVENTION

The new cultivar is the product of a planned breeding program under the direction of the inventors, David Kerley, Priscilla Kerley and Timothy Kerley, all citizens of the United Kingdom. The objective of the breeding program was to produce new, compact pot-type *Primula vulgaris* cultivars with abundant double flowers for commercial ornamental purposes. The new cultivar resulted from crossing of two unpatented, unnamed proprietary *Primula vulgaris* varieties during March of 2004. The selection of the new variety 'Kerbelred' was made in March 2005, by the inventors at a research greenhouse located in Cambridge, UK.

Asexual reproduction of the new cultivar 'KERBELRED' by division was first performed at the same research greenhouse in Cambridge, UK during the Summer of 2005, and subsequently by tissue culture the Roelofarendsveen, the Netherlands. Both methods have shown that the unique features of this cultivar are stable and reproduced true to type in successive generations.

SUMMARY OF THE INVENTION

The cultivar 'KERBELRED' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KERBELRED' These characteristics in combination distinguish 'KERBELRED' as a new and distinct *Primula* cultivar:

1. Deep red flower color
2. Early blooming
3. Enlarged sepals behind the flower
4. Unique fully double flowers 5. Large flowers
6. Strong peduncles
7. Good propagation rate in tissue culture

PARENT COMPARISON

Plants of the new cultivar 'KERBELRED' are similar to plants of the seed parent variety, in most horticultural characteristics. However, plants of the new cultivar produce double, sterile flowers, whereas the seed parent produces single, fertile flowers. Additionally, the new variety produces flowers over a longer period of time than the seed parent, and individual flowers on the new variety last longer.

Plants of the new cultivar 'KERBELRED' are similar to plants of the pollen parent variety, in most horticultural characteristics. However, plants of the new cultivar produce double, sterile flowers, whereas the pollen parent produces single, fertile flowers. Additionally, the new variety produces flowers over a longer period of time than the pollen parent, and individual flowers on the new variety last longer.

COMMERCIAL COMPARISON

Plants of the new variety can be compared to plants of the *Primula vulgaris* cultivar 'Roy Cope', not patented. In side-by-side comparisons conducted in Over, Cambridge, United Kingdom, plants of the new *Primula* differed from plants of the cultivar 'Roy Cope' in the following characteristics:

1. Plants of the new *Primula* were more compact than plants of the cultivar 'Roy Cope'.
2. Plants of the new *Primula* had strong upright peduncles whereas plants of the cultivar 'Roy Cope' had weak arching peduncles.
3. Plants of the new *Primula* had larger flowers than plants of the cultivar 'Roy Cope'.
4. Plants of the new *Primula* had bright, deep red-colored flowers whereas plants of the cultivar 'Roy Cope' had purplish-red-colored flowers.

5. Plants of the new *Primula* had larger sepals than plants of the cultivar 'Roy Cope'.
6. Plants of the new *Primula* had strong upright peduncles whereas plants of the cultivar 'Roy Cope' had long weak arching peduncles.
7. Plants of the new *Primula* are significantly earlier flowering than 'Roy Cope'.

Plants of the 'KERELRED' can be compared to plants of the *Primula vulgaris* cultivar 'Captain Blood', not patented. In side-by-side comparisons conducted in Over, Cambridge, United Kingdom, plants of the new *Primula* differed from plants of the cultivar 'Captain Blood' in the following characteristics:

1. Plants of the new *Primula* had larger flowers than plants of the cultivar 'Captain Blood'.
2. Plants of the new *Primula* had larger sepals than plants of the cultivar 'Captain Blood'.
3. Plants of the new *Primula* flowered earlier than plants of the cultivar 'Captain Blood'.
4. Plants of the new *Primula* had bright, deep red-colored flowers whereas plants of the cultivar 'Captain Blood' had dark red-colored flowers.
5. Plants of the new *Primula* had smaller leaves than plants of the cultivar 'Captain Blood'.

BRIEF DESCRIPTION OF THE PHOTOGRAPHS

The accompanying photograph in FIG. 1 illustrates in full color typical plants of 'KERBELRED' grown in Over, Cambridge, United Kingdom, in a glass-covered greenhouse and under commercial production practices during the spring.

Plants were about four to five months old when the photographs were taken. During the production of the plants, day temperatures ranged from 5 to 15 degree C. and night temperatures ranged from 2 to 12 degree C.

Figure 2:
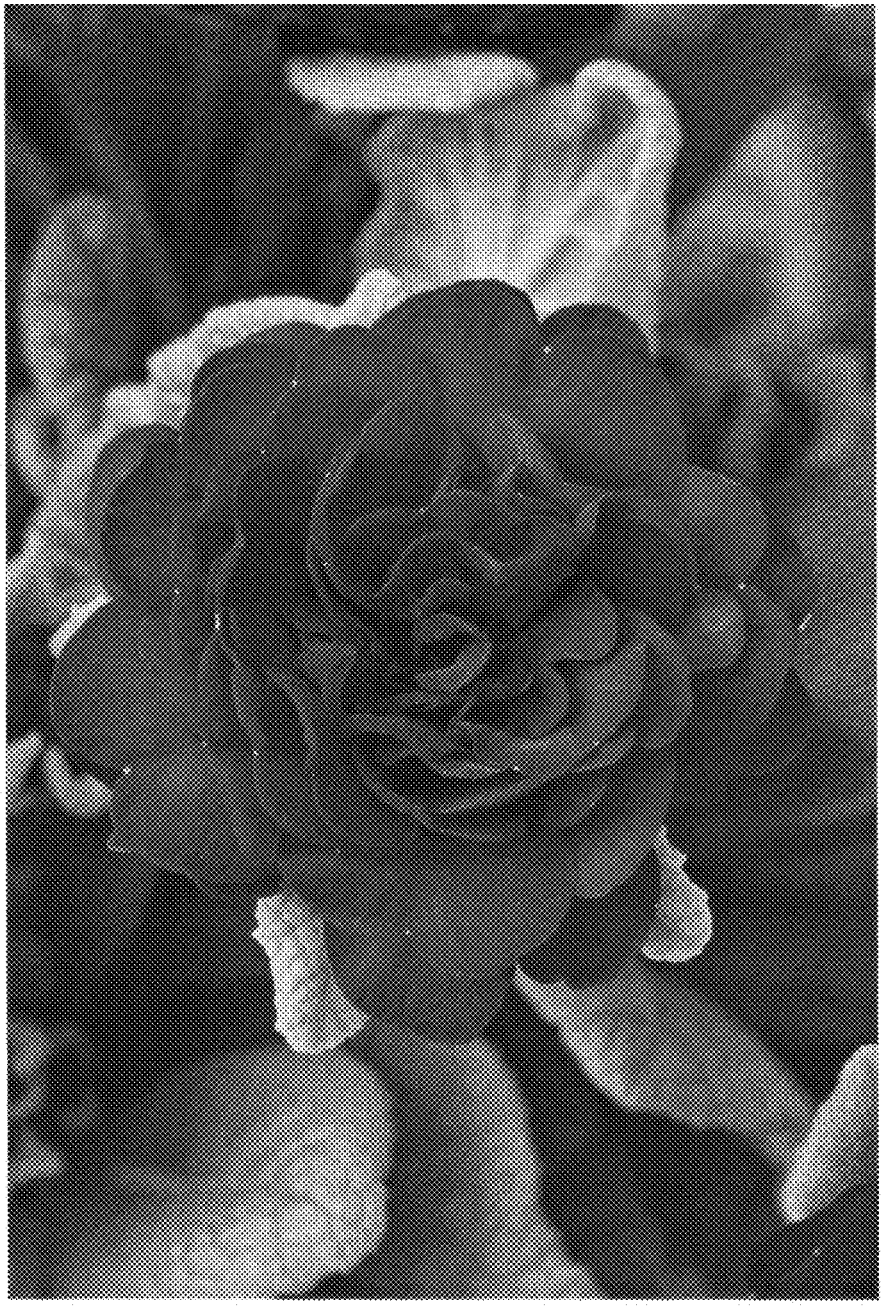

FIG. 2 illustrates a close up of a typical flower of 'KERBELRED'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 1995 except where general terms of ordinary dictionary significance are used. The following observations and measurements describe 'KERBELRED' plants grown under commercial production practices during the spring in Cambridge, United Kingdom. During the production of the plants, day temperatures ranged from 5 to 15 degree C. and night temperatures ranged from 2 to 12 degree C. No chemical or photoperiodic treatments were given. Measurements and numerical values represent averages of typical flowering types.

Botanical classification: *Primula vulgaris* 'KERBELRED'.

Age of the plant described: Approximately 4 to 5 months in an 11 cm pot.

PROPAGATION

Method: Tissue culture.

Time to initiate roots: About four weeks at 20° C.

Time to produce a rooted young plant: About six weeks at 20° C.

Root description: Fine, fibrous, free branching, colored near RHS White 155A.

PLANT

Growth habit: Upright, compact and uniform. Inverted triangle. Vigorous.

Height: Approximately 10 to 13 cm.

Plant spread: Approximately 25 cm.

Branching characteristics: No branches, foliage emerges basally.

FOLIAGE

Leaf:

*Arrangement.*—Basal, simple.

*Average length.*—Approximately 12 to 16 cm.

*Average width.*—Approximately 3.5 to 4.7 cm.

*Shape of blade.*—Oblanceolate.

*Apex.*—Obtuse.

*Base.*—Acute.

*Attachment.*—Petioled.

*Margin.*—Slightly crenate, irregularly. Somewhat undulate.

*Texture of top surface.*—Glabrous, slightly rugose.

*Texture of bottom surface.*—Veins prominent, veins pubescent.

*Color.*—Developing foliage upper side: Near RHS Green 143A. Developing foliage under side: Near RHS Yellow-Green 144A. Mature foliage upper side: Near RHS Yellow-Green 147A. Mature foliage under side: Near RHS Yellow-Green 147B.

*Venation.*—Type: Pinnate. Venation color upper side: Near RHS Yellow-Green 145C and 145D. Venation color under side: Near RHS Yellow-Green 145C.

Petiole:

*Length.*—Approximately 2.0 to 2.5 cm.

*Diameter.*—6 to 9 mm.

*Color.*—Upper Surface: Near RHS Yellow-Green 149D, occasionally irregularly tinged Red-Purple 59D. Lower Surface: Near RHS Yellow-Green 145C and 145D, occasionally irregularly tinged Red-Purple 59D.

*Texture all surfaces.*—Glabrous, slightly hirsute margins.

FLOWER

Bloom period: Recurrent flowering during the Spring under United Kingdom outdoor conditions. Very free flowering.

Inflorescence: Solitary, rounded double flowers, upright and outwardly facing.

Persistent or self-cleaning: Persistent.

Fragance: None.

Flowers per plant: Approximately 50 flowers and buds.

Flower bud:

*Bud color.*—Near RHS Yellow-Green 144A and 144B.

*Bud length.*—Average 10 to 15 mm.

*Bud diameter.*—Average 5 to 8 mm.

*Shape.*—Ovoid.

Individual flower:

*Flower size.*—Depth: Approximately 2.0 to 2.7 cm. Diameter: Approximately 3.5 to 4.2 cm.

Petals:

*Quantity.*—24 to 42 per flower, arranged in several concentric whorls.
*Shape.*—Obcordate.
*Length.*—Approximately 14 to 21 mm.
*Width.*—Approximately 9 to 18 mm.
*Margin.*—Entire.
*Apex.*—Emarginate.
*Texture.*—Upper and lower surfaces slightly corrugated, glabrous, satiny appearance.
*Color.*—When opening, upper surface: Near RHS Red-Purple 59A, but darker. When opening, lower surface: Near RHS Red-Purple 59A and 59B. Fully opened, upper surface: Between RHS Red-Purple 59A and Red 46A, but, more intense. Closer to 46A with age. Fully opened, lower surface: Between RHS Red-Purple 59A and Red 46A. Fading, all surfaces: No significant fading, closest to Red 46A.

Sepals:

*Quantity.*—5 or 6.
*Arrangement.*—Single whorl, fused at base.
*Length.*—Approximately 1.7 to 2.2 cm.
*Width.*—Approximately 0.6 to 1.0 cm.
*Color.*—Near RHS Yellow-Green 144A.
*Shape.*—Oblong.
*Apex.*—Obtuse.
*Base.*—Fused.
*Texture, all surfaces.*—Glabrous, rugose.
*Aspect.*—Occasionally twisted along the length.

Peduncle:

*Peduncle length.*—Approximately 6 to 10 cm.
*Peduncle diameter.*—Approximately 0.2 to 0.25 cm.
*Orientation.*—Erect.
*Strength.*—Strong.
*Aspect.*—Upright with outward curve.
*Color.*—Near RHS Yellow-Green 145D, streaked irregularly Red-Purple 59D.
*Texture.*—Pubescent.

REPRODUCTIVE ORGANS

Reproductive organs: Have not been observed. Flowers are sterile.

OTHER CHARACTERISTICS

Disease resistance: Neither resistance nor susceptibility to diseases or pests has been observed in this variety.

Temperature tolerance: Tolerates high temperature to at least 28° C. Tolerates low temperatures to −15° C.

Fruit/seed production: Fruit and seed production not observed, flowers are sterile.

What is claimed is:

1. A new and distinct cultivar of *Primula* plant named 'KERBELRED' as herein illustrated and described.

* * * * *